(12) United States Patent
Nakanishi et al.

(10) Patent No.: US 8,609,806 B2
(45) Date of Patent: Dec. 17, 2013

(54) PHOSPHORUS-CONTAINING PHENOL COMPOUND, PRODUCTION METHOD THEREFOR, AND CURABLE RESIN COMPOSITONS AND CURED PRODUCTS USING THE COMPOUND

(75) Inventors: Tetsuya Nakanishi, Sodegaura (JP); Hideyasu Asakage, Sodegaura (JP); Seigo Takuwa, Sodegaura (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 250 days.

(21) Appl. No.: 12/998,078

(22) PCT Filed: Sep. 2, 2009

(86) PCT No.: PCT/JP2009/065615
§ 371 (c)(1),
(2), (4) Date: Mar. 14, 2011

(87) PCT Pub. No.: WO2010/032650
PCT Pub. Date: Mar. 25, 2010

(65) Prior Publication Data
US 2011/0166260 A1 Jul. 7, 2011

(30) Foreign Application Priority Data
Sep. 16, 2008 (JP) .................................. 2008-237165

(51) Int. Cl.
C08G 59/62 (2006.01)
C08G 59/18 (2006.01)
C08L 63/00 (2006.01)
C07F 9/6571 (2006.01)

(52) U.S. Cl.
USPC ............... 528/421; 528/96; 528/98; 528/167; 528/219; 528/398; 528/418; 568/8; 568/12; 568/17

(58) Field of Classification Search
USPC ............ 568/8, 12, 17; 523/435, 451; 528/96, 528/98, 167, 219, 398, 418, 421
See application file for complete search history.

(56) References Cited

FOREIGN PATENT DOCUMENTS

| | | | |
|---|---|---|---|
| CN | 101108864 | 1/2008 | |
| JP | 60-126293 | 7/1985 | |
| JP | 10-244761 | 9/1998 | |
| JP | 3092009 | 7/2000 | |
| JP | 2000-212391 | 8/2000 | |
| JP | 3108412 | 9/2000 | |
| JP | 2000-309624 | 11/2000 | |
| JP | 2001-040181 | 2/2001 | |
| JP | 2002-249540 | 9/2002 | |
| JP | 2003-128753 | 5/2003 | |
| JP | 3642403 | 2/2005 | |
| JP | 2009-185087 | 8/2009 | |
| KR | 10-0805198 B1 * | 2/2008 | ............ C07F 9/6571 |
| WO | WO 2009/060987 | 5/2009 | |

OTHER PUBLICATIONS

Machine translation of KR 10-0805198 B1, provided by the KIPO website (no. date).*
Campbell et al., "Duality in the Chemical Character of Secondary Phosphine Oxides," Chemical Communication, p. 505-506 (1966).
Magdeyev et al., "On the Products of the Reaction of Diphenylphosphinous Acid and the Hydrochloride Thereof with p-Benzoquinne", Zhurnal Obshchey Khimii, 42(11), p. 2415-2418 (1972).
International Search Report dated Dec. 8, 2009 issued in corresponding PCT Application No. PCT/JP2009/065615.

* cited by examiner

*Primary Examiner* — Michael J Feely
(74) *Attorney, Agent, or Firm* — Kenyon & Kenyon LLP (57) ABSTRACT

To provide phosphorus-containing epoxy resins and phosphorus-containing epoxy resin compositions having high levels of appearance, yield and economic efficiency and cured products thereof that are used for various applications. A phosphorus-containing phenol compound represented by Formula (3) obtained by reacting a compound represented by Formula (2) with a compound represented by Formula (1), wherein in the peak area (A) of the component represented by Formula (1) on a chromatogram measured under specific conditions by gel permeation chromatography, peak area (B) on the high-molecular-weight side of the component of Formula (1), and total area (C) of peak area (A) and peak area (B), the value obtained by dividing peak area (B) by total area (C) is 8 area % or less, and epoxy resin compositions and cured products comprising the phosphorus-containing phenol compound as an essential ingredient.

5 Claims, 2 Drawing Sheets

Fig.2

|  | RETENTION TIME [min] | HIGHT [mV] | AREA [mV·sec] | AREA [%] |
|---|---|---|---|---|
| (A) | 30.300 | 259.522 | 9791.432 | 96.123 |
| (B) | 28.340 | 3.279 | 394.903 | 3.877 |
| TOTAL |  | 262.801 | 10186.335 | 100.000 |

PHOSPHORUS-CONTAINING PHENOL COMPOUND, PRODUCTION METHOD THEREFOR, AND CURABLE RESIN COMPOSITONS AND CURED PRODUCTS USING THE COMPOUND

This application is a national stage application of International Application No. PCT/JP2009/065615, filed 2 Sep. 2009, which claims priority to Japanese Application No. 2008-237165, filed 16 Sep. 2008, which is incorporated by reference in its entirety.

TECHNICAL FIELD

The present invention relates to a phosphorus-containing phenol compound effectively used in epoxy resin compositions used for the production of copper-clad laminates, film materials, resin coated copper foils, and the like for electronic circuit boards and sealants, molding materials, casting materials, adhesives, insulating coating materials, and the like used for electronic parts, production methods therefor, and phosphorus-containing curable resin compositions and cured products comprising the compound as an essential ingredient and an epoxy resin.

BACKGROUND

Epoxy resins are widely used for electronic parts, electrical devices, automobile parts, FRP, sporting goods, and the like, due to their excellent adhesion, heat resistance, and molding properties. In particular, it is required that copper-clad laminates and sealants used in electronic parts and electrical devices must be flame retardant so as to assure safety, i.e., prevention of fire and delay of combustion. Brominated epoxy resins and the like having these properties have been used. The brominated epoxy resins are considered to be useful electronic and electrical materials because flame retardancy is imparted by introduction of a halogen, especially bromine and the epoxy group exhibits high reactivity and imparts an excellent curing property.

However, there is a recent tendency that electrical devices are developed such that the size and weight of the devices are reduced and circuits therein are miniaturized. Under the situation where these demands must be satisfied, halides having a high specific gravity are not preferable from the point of reduction in weight. In addition, after the use thereof at a high temperature for a long period of time, separation of halides may occur. It may lead to corrosion of fine wirings. Further, as harmful compounds such as halides and the like are produced when used electronic parts and electrical devices are burned, use of halogens is being considered as a problem from the view point of assuring the environment safety.

Recently, a large number of inorganic materials such as aluminum hydroxide, phosphorus compounds, nitrogen compounds, and the like as substituting materials have been studied. In particular, among them, flame retardant formulations using a phosphorus compound have been studied recent years. Addition of phosphates, red phosphorus, and the like as phosphorus sources which impart flame retardancy to epoxy resins is disclosed. Phosphates affect the anti-migration property because phosphates are hydrolyzed to release acids. Although red phosphorus exhibits high flame retardancy, it is designated as a hazardous substance by the Fire Defense Law and a trace amount of a phosphine gas is produced under atmosphere at high temperature and high humidity. Therefore, it has been studied to use a compound represented by Formula 3 and disclosed in Non-patent literature publications 1 and 2 and Patent publication 1 so as impart flame retardancy to epoxy resins.

Formula 3

Regarding imparting flame retardancy to resins using the compound represented by Formula 3, a phosphorus-containing epoxy resin obtained by reacting the compound with an epoxy resin described in Patent publication 2 and an example of applying the compound to a cyanate resin described in Patent publication 3 obtained by the reaction with a cyanate ester compound were known. It is disclosed that flame retardancy is imparted by modifying the resin with phosphorus in the methods. As described above, the compound represented by Formula 3 is extremely important in the means for imparting flame retardancy without using a halogen.

A method for producing the compound represented by Formula 3 is specifically described in, for example, Non-patent literature publication 2 and Patent publication 1. However, a recrystallization step is necessary to increase the purity of the compound in the method. The yield of the compound is low by the method. Therefore, the compound could not be prepared with high purity and in sufficient yield by any conventional methods. In addition, as equipments must be used for a long period of time during the recrystallization step, productivity is low.

The object to increase the productivity of the compound represented by Formula 3 is disclosed in Patent publication 4. The object is achieved by a method for producing a flame retardant epoxy resin which comprises reacting an epoxy resin with a compound represented by Formula 2 and a compound represented by Formula 1 in the presence of an organic solvent. It is described that after the compound represented by Formula 3 is obtained by reacting the compound represented by Formula 2 with the compound represented by Formula 1, the epoxy resin is further reacted with the above reaction product to obtain a phosphorus-containing epoxy resin. As the compound represented by Formula 2 and the compound represented by Formula 1 per se charged into the system can be introduced into the resin, the yield of the compound represented by Formula 3 is increased. However, there are problems that the resin appearance, curing reactivity, heat resistance, anti-migration property, and the like are influenced by side-products produced by the reactions.

The inventors of the present application keenly studied phosphorus-containing epoxy resins and found that the physical properties of a phosphorus-containing epoxy resin obtained by reacting the phosphorus-containing phenol compound represented by Formula 3 with an epoxy resin at the predetermined molar ratio are significantly influenced by the quality of the phosphorus-containing phenol compound and filed Patent Application No. 2008-023014 and Patent Application No. 2008-023015. Namely, due to the presence of a trace amount of a reaction side-product, such as a phosphorus-containing mono-phenol compound, as an impurity contained in the compound represented by Formula 3, the curing time of the phosphorus-containing epoxy resin is remarkably prolonged and adhesion property thereof becomes poor. As the curing reactivity is changed by the presence of an impurity component, it was predicted that problems of reduction in adhesion property and heat resistance of the resins, due to the insufficient curing level and declined productivity, due to curing time delay would occur. It was also predicted that problems of reduction in adhesion force and insulation failure would occur in the advanced electronic material field in which electronic circuits are being miniaturized, depending on the curing reaction conditions. Therefore, it is clear that the purity of the compound represented by Formula 3 which is a material for phosphorus-containing epoxy resins is very important.

Considering the above points, when flame retardancy is imparted to epoxy resins, it is necessary to use the high-purity phosphorus-containing phenol compound represented by Formula (3). However, a conventional method for obtaining the phosphorus-containing phenol compound with high purity and in high yield was not known.

Other than modification of epoxy resins with phosphorus, a method for simply adding phosphorus to a curable epoxy resin composition was disclosed as a method for imparting flame retardancy using the compound represented by Formula 3. Patent publications 5 to 8 describe the method. The publications also describe that curable resin compositions obtained by adding the predetermined amount of the compound represented by Formula 3 to an epoxy resin, a curing agent, and a curing accelerator and cured products thereof exhibit flame retardancy. Patent publication 8 describes that flame retardancy and heat resistance are increased by adding the compound to an epoxy resin. However, as the compound represented by Formula 3 exhibits poor solvent solubility and crystals thereof are easily formed, the compound can be added only in an amount such that crystals thereof are not formed in the technical filed where miniaturization and uniform curing are required, such as the electronic material field. Therefore, it was not considered that the compound can be a main component which imparts flame retardancy. There was a problem that the compound can be only used as an auxiliary compound for imparting flame retardancy.

Non-Patent Literature Publications

Non-patent literature publication 1: I. G. M. Campbell and I. D. R. Stevens, Chemical Communications, Pages 505-506 (1966)

Non-patent literature publication 2: (Zh. Obshch. Khim.), 42(11), Pages 2415-2418 (1972)

Patent Publications

Patent publication 1: Kokai No. 60-126293
Patent publication 2: Patent No. 3092009
Patent publication 3: Kokai No. 2003-128753
Patent publication 4: Patent No. 3642403
Patent publication 5: Kokai No. 2000-212391
Patent publication 6: Patent No. 3108412
Patent publication 7: Kokai No. 2001-040181
Patent publication 8: Kokai No. 2002-249540

DISCLOSURE OF THE INVENTION

The object of the present invention is to provide the phosphorus-containing phenol compound represented by Formula (3) by a method for producing the same with high purity and in high yield. Another object of the present invention is to provide curable resin compositions and cured products comprising the phosphorus-containing phenol compound obtained in the present invention as an essential ingredient.

The inventors of the present application keenly studied to solve the above problems and found that the purity, yield, and the like of the phosphorus-containing phenol compound represented by Formula (3) are remarkably affected by the purity of the compound represented by Formula (1) used in the reaction with the compound represented by Formula (2). The cause thereof is that the compound represented by Formula (1) is not a stable compound and even that industrially produced or commercially available as a reagent contains a large amount of impurities.

Formula 1

The inventors of the present application found that the compound represented by Formula (1) easily changes over time, that if it is stored under normal conditions at room temperature and the like, some of the compounds are converted to other compounds having a large molecular weight, and that these polymer components cause a side reaction in the process for producing the phosphorus-containing phenol compound represented by Formula (3), which leads to reduction in purity thereof. Consequently, the inventors of the present application found that the phosphorus-containing phenol compound represented by Formula (3) can be obtained with high purity and in high yields using the compound with a predetermined amount or less of the polymer compounds contained in the compound represented by Formula (1). They also found that epoxy resin compositions comprising the obtained phosphorus-containing phenol compound as an essential ingredient do not affect productivity, namely do not cause insufficient curing, curing time delay, and the like and completed the present invention.

In addition, the phosphorus-containing phenol compound obtained by the production method of the present invention exhibits excellent solubility at the time of thermal curing, whereby a uniformly cured product that cannot be obtained by conventional production methods can be obtained. This is because the production method of the present invention does not need a recrystallization step, and thus the crystallization degrees of the phosphorus-containing phenol compounds represented by Formula (3) are different.

Namely, the present invention relates to:

(1) A phosphorus-containing phenol compound represented by Formula (3) obtained by reacting a compound represented by Formula (2) with a compound represented by Formula (1), wherein in peak area (A) on a chromatogram measured under specific conditions by gel permeation chromatography, peak area (B) on the high-molecular-weight side of the component of (A), and total area (C) of peak area (A) and peak area (B), the value obtained by dividing peak area (B) by total area (C) is 8 area % or less;

(Measuring Conditions for Gel Permeation Chromatography):

an analytical column having an exclusion limit molecular weight of 400,000, a number of theoretical stages of 16,000, and a length of 30 cm, an analytical column having an exclusion limit molecular weight of 60,000, a number of theoretical stages of 16,000, and a length of 30 cm, and an analytical column having an exclusion limit molecular weight of 10,000, a number of theoretical stages of 16,000, and a length of 30 cm connected in series are used, the temperature in a column room is adjusted to 40° C., an ultraviolet-visible detector is used as a detector, the measured wavelength is 400 nm, the flow rate of tetrahydrofuran as an eluent is 1 ml/min, and a sample is prepared using a tetrahydrofuran solution containing 1% of the compound represented by Formula (1) for the determination.

Formula 1

Formula 2

Formula 3

(2) A method for producing the phosphorus-containing phenol compound according to (1) comprising filtering a solution of a compound represented by Formula (1) so that in peak area (A) of on a chromatogram, peak area (B) on the high-molecular-weight side of the component of (A), and total area (C) of peak area (A) and peak area (B), the value obtained by dividing peak area (B) by total area (C) is 8 area % or less and reacting the compound represented by Formula (1) which had been subjected to solution filtration with a compound represented by Formula (2).

(3) A curable resin composition comprising the phosphorus-containing phenol compound according to (1) as an essential ingredient and an epoxy resin.

(4) A curable resin composition comprising the phosphorus-containing phenol compound obtained by the method for producing a phosphorus-containing compound according to (2) as an essential ingredient and an epoxy resin.

(5) A cured product prepared by curing the curable resin composition according to (3) or (4).

The phosphorus-containing phenol compound represented by Formula (3) which exhibits an excellent color can be obtained with high purity and in high yield without performing a complicated procedural step such as a recrystallization step or the like by using the compound represented by Formula (1) whose value obtained by dividing peak area (B) that is determined under specific conditions by gel permeation chromatography by total area (C) is 8 area % or less. In addition, the present invention can provide curable resin compositions comprising the obtained phosphorus-containing phenol compound as an essential ingredient and cured products thereof that are excellent in color and appearance.

MODES FOR CARRYING OUT THE INVENTION

The phosphorus-containing phenol compound of the present invention can be obtained by reacting the compound represented by Formula (1) with the compound represented by Formula (2). The polymer component content in the compound represented by Formula (1) determined under specific conditions by gel permeation chromatography is 8 area % or less, based on the total peak area.

The inventors of the present application were able to obtain the phosphorus-containing phenol compound represented by Formula (3) with high purity and in high yield by reacting the compound represented by Formula (1) from which the polymer components were removed with the compound represented by Formula (2) and completed the invention of the present application. Further, the inventors of the present application found that curable resin compositions prepared by adding this phosphorus-containing phenol compound as an essential ingredient to an epoxy resin exhibit the same or more excellent color, appearance, curing properties and the like, compared with those produced by conventional methods, that epoxy resin compositions exhibit excellent solubility at the time of thermal curing, and that uniformly cured products that cannot be obtained by conventional production methods can be obtained, and they completed the present invention. The phosphorus-containing phenol compound of the present invention is preferably used in electronic circuit boards, sealant materials, casting materials, and the like.

When the phosphorus-containing phenol compound represented by Formula (3) is obtained using the compound represented by Formula (1) from which the polymer components had been removed, the polymer component content in the compound represented by Formula (1) is 8 area % or less, preferably 6 area % or less, more preferably 4 area % or less. The phosphorus-containing phenol compound represented by Formula (3) obtained by reacting the compound represented by Formula (1) having the content of more than 8 area % with the compound represented by Formula (2) exhibits a poor color. Epoxy resin compositions comprising the phosphorus-containing phenol compound as an essential ingredient and cured products thereof exhibit poor color and are turbid. In addition, there are problems such as significant curing time delay, insufficient curing, and an adverse effect on productivity.

The polymer component content in the compound represented by Formula (1) can be reduced by a purification step after production of the compound, such as extraction, washing, recrystallization, distillation, sublimation, or the like. If the content becomes more than 8 area %, due to a change over time, it can be reduced to 8 area % or less by the purification step after production of the compound, such as extraction, washing, recrystallization, distillation, sublimation, or the like. In particular, filtration to remove the polymer components using the difference in solubility in a solvent between the compound represented by Formula (1) and the polymer components is an easy purification method.

The method for producing the phosphorus-containing phenol compound represented by Formula (3) will be specifically exemplified. Each of the compound represented by Formula (1) and the compound represented by Formula (2) is dissolved in a solvent in a different container. While the solution of the compound represented by Formula (1) is subjected to filtration to remove the polymer components with a filter, the obtained filtrate is directly dropped into the solution of the compound represented by Formula (2) for ten minutes to ten hours, preferably ten minutes to five hours, more preferably ten minutes to three hours to proceed a consecutive reaction, whereby the compound represented by Formula (1) can be provided to the reaction system without additional formation of the polymer components.

In order to prevent the polymer components contained in the compound represented by Formula (1) from being dissolved and passed through the filter without being separated by filtration, the dissolution temperature and the filtration temperature are 60° C. or lower, preferably 40° C. or lower. The reaction is consecutively proceeded by dropping the filtered solution of the compound represented by Formula (1) under the condition that the temperature of the solution of the compound represented by Formula (2) is maintained at 60 to 150° C. and the compounds are reacted at a temperature maintained at 60° C. or higher, preferably 80° C. or higher, more preferably 100° C. or higher to provide the phosphorus-containing phenol compound.

The solvent used for dissolving the compounds of Formula (1) and Formula (2) is inert to both the compounds and preferably has a boiling point of 35 to 150° C. and a dielectric constant of 10 or less, more preferably 5 or less. Specific examples thereof include hydrocarbons such as toluene, xylene, n-hexane, and the like and ethers such as dioxane and the like. The solvent is not limited to those described herein and two or more thereof can be used. Solvents having a carbonyl group such as ketones are not preferable because they react with the compound represented by Formula (2).

In addition, the solvent dissolving the compound of Formula (1) may be different from the solvent dissolving the compound of Formula (2). In either case, the difference in solubility between the compound represented by Formula (1) and the polymer components is important. The important factors to control the difference are selection of the type of a solvent dissolving the compound represented by Formula (1) and the dissolution temperature. Further, the means for adjusting the polymer component content is not limited to filtration, but a purification method such as recrystallization or sublimation may be used.

The compound represented by Formula (3) is precipitated after completion of the reaction, and thus the compound represented by Formula (3) is separated by a solid-liquid separator. At this time, a trace amount of the compound represented by Formula (1) or (2) is dissolved in the solvent. The purity thereof can be further increased by washing the separated compound represented by Formula (3) with the solvent. In addition, the amount of ionic impurities can be reduced by washing with water.

Epoxy resins added to obtain curable resin compositions comprising the phosphorus-containing phenol compound obtained with high purity and in high yield as an essential ingredient preferably have at least two glycidyl groups in one molecule. Specific examples thereof include epoxy resins produced from a phenol compound with epihalohydrin such as polyfunctional phenol resins including Epotohto YDC-1312 and Epotohto ZX-1027 (hydroquinone type epoxy resins, manufactured by Tohto Kasei Co., Ltd.), Epotohto ZX-1251 (a bisphenol type epoxy resin, manufactured by Tohto Kasei Co., Ltd.), Epotohto YD-127, Epotohto YD-128, Epotohto YD-8125, Epotohto YD-825GS, Epotohto YD-011, Epotohto YD-900, and Epotohto YD-901 (BPA type epoxy resins, manufactured by Tohto Kasei Co., Ltd.), Epotohto YDF-170, Epotohto YDF-8170, Epotohto YDF-870GS, and Epotohto YDF-2001 (BPF type epoxy resins, manufactured by Tohto Kasei Co., Ltd.), Epotohto YDPN-638 (a phenol novolac type epoxy resin, manufactured by Tohto Kasei Co., Ltd.), Epotohto YDCN-701 (a cresol novolac type epoxy resin, manufactured by Tohto Kasei Co., Ltd.), Epotohto ZX-1201 (a bisphenol fluorene type epoxy resin, manufactured by Tohto Kasei Co., Ltd.), NC-3000 (a biphenyl aralkylphenol type epoxy resin, manufactured by Nippon Kayaku Co., Ltd.), EPPN-501H and EPPN-502H (polyfunctional epoxy resins, manufactured by Nippon Kayaku Co., Ltd.), Epotohto ZX-1355 (a naphthalenediol type epoxy resin, manufactured by Tohto Kasei Co., Ltd.), Epotohto ESN-155, Epotohto ESN-185V, and Epotohto ESN-175 ($\beta$-naphthol aralkyl type epoxy resins, manufactured by Tohto Kasei Co., Ltd.), Epotohto ESN-355 and Epotohto ESN-375 (dinaphthol aralkyl type epoxy resins, manufactured by Tohto Kasei Co., Ltd.), Epotohto ESN-475V and Epotohto ESN-485 ($\alpha$-naphthol aralkyl type epoxy resins, manufactured by Tohto Kasei Co., Ltd.), and the like, epoxy resins produced from an amine compound with epihalohydrin such as Epotohto YH-434 and Epotohto YH-434GS (diaminodiphenylmethane tetraglycidylamines, manufactured by Tohto Kasei Co., Ltd.) and the like, epoxy resins produced from a carboxylic acid with epihalohydrin such as Epotohto YD-171 (a dimer acid type epoxy resin, manufactured by Tohto Kasei Co., Ltd.) and the like, phosphorus-containing epoxy resins such as Epotohto FX 289B and Epotohto FX-305 (phosphorus-containing epoxy resins, manufactured by Tohto Kasei Co., Ltd.), Phenotohto ERF-001 (a phosphorus-containing epoxy resin, manufactured by Tohto Kasei Co., Ltd.) and the like. However, the epoxy resin is not limited thereto, but two or more thereof can be used in combination.

An excess amount of the epoxy resin may be added with respect to the phosphorus-containing phenol compound, if necessary and a curing agent may be used for reaction with the excess epoxy groups for the curable resin composition comprising the phosphorus-containing phenol compound of the present invention as an essential ingredient and an epoxy resin. Generally used curing agents for epoxy resins such as various phenol resins, acid anhydrides, amines, hydrazides, acid polyesters, aminotriazine phenols, and the like may be used. These curing agents may be used alone or two or more thereof may be used.

A curing accelerator such as a tertiary amine, quaternary ammonium salt, a phosphine, an imidazole and the like may be added to the curable resin composition comprising the phosphorus-containing phenol compound of the present invention as an essential ingredient and an epoxy resin.

An organic solvent may be used as a viscosity modifier for the curable resin composition comprising the phosphorus-containing phenol compound of the present invention as an essential ingredient and an epoxy resin. The organic solvent that may be used includes ethers such as ethylene glycol monomethyl ether and the like, ketones such as acetone, methyl ethyl ketone and the like, alcohols such as methanol, ethanol, and the like, aromatic hydrocarbons such as benzene, toluene, and the like. One or more of these solvents may be used. The solvent may be added so as to provide an epoxy resin concentration of 30 to 80 wt %.

A filler may be added to the curable resin composition comprising the phosphorus-containing phenol compound of the present invention as an essential ingredient and an epoxy resin, if necessary. Specific examples thereof include inorganic fillers such as aluminum hydroxide, magnesium hydroxide, talc, sintered talc, clay, kaolin, titanium oxide, glass powder, fine silica powder, molten silica, crystalline silica, silica balloons, and the like. However, pigments and the like may be added. The reason for using a general inorganic filler is to increase impact resistance.

In addition, when a metal hydroxide such as aluminum hydroxide, magnesium hydroxide or the like is used, it functions as a flame retardant, and flame retardancy can be obtained, if the phosphorus content is small. In particular, if the formulation amount is 10% or more, an effect on impact resistance is high. However, if the formulation amount is more than 150%, the adhesion property which is required in application thereof to laminates is reduced. In addition, fibrous fillers such as silica, glass fibers, pulp fibers, synthetic fibers, ceramic fibers, and the like, and organic fillers such as fine particle rubbers, thermoplastic elastomers, and the like may be added to the above resin compositions.

Materials for electronic circuit boards obtained using the above curable resin compositions include resin sheets, resin-coated metal foils, prepregs, and laminates. The method for producing the resin sheets is not particularly limited. However, the resin sheets are produced by a method generally called the casting method which comprises coating the above phosphorus-containing epoxy resin composition on a carrier film such as a polyester film, a polyimide film or the like which is not dissolved in the curable resin composition so as to preferably have a thickness of 5 to 100 μm, and then heating the same at 100 to 200° C. for 1 to 40 minutes to form the composition into a sheet shape. If a surface of the sheet on which the phosphorus-containing epoxy resin composition is coated is treated with a releasing agent, the produced resin sheet can be easily released. It is preferable that the resin sheet is formed so to have a thickness of 5 to 80 μm.

Next, the resin-coated metal foils obtained using the above curable resin composition will be explained. A metal foil such as a single, alloy or composite foil of copper, aluminum, brass, nickel, or the like may be used. The metal foil having a thickness of 9 to 70 μm is preferably used. A method for producing a resin-coated metal foil from a flame retardant resin composition comprising the phosphorus-containing phenol compound and the metal foil is not particularly limited. For example, it can be obtained by coating a resin varnish prepared by dissolving the above curable resin composition in a solvent such that the varnish has a low viscosity, using a roll coater or the like and heating and drying the varnish such that the resin component is semicured (at B-stage) to form a resin layer. The resin components can be semicured by heating and drying at, for example, 100 to 200° C. for 1 to 40 minutes. It is preferable to prepare the resin-coated metal foil such that the rein portion thereof has a thickness of 5 to 110 μm.

Next, the prepregs obtained using the above curable resin composition will be explained. Woven or nonwoven fabrics of inorganic fibers of glass or the like, organic fibers of a polyester, polyamine, acrylic polymer, polyimide, Kevlar or the like may be used as a sheet substrate. However, the sheet substrate is not limited thereto. A method for producing a prepreg from the curable resin composition and the substrate is not particularly limited. For example, it is obtained by immersing the substrate in a resin varnish prepared by dissolving the epoxy resin composition in a solvent so as to have the predetermined viscosity, and then heating and drying the same such that the resin components are semicured (at B-stage), for example, at 100 to 200° C. It is preferable that the amount of the resin in the prepreg is 30 to 80 wt % with respect to the total weight of the prepreg.

Next, a method for producing a laminate using the above resin sheet, the resin-coated metal foil, the prepreg or the like will be explained. When a laminate is formed using the prepreg, one or more layers of the prepreg are laminated, a metal foil is provided on either side or both sides to constitute a laminate, and the laminate is heated and pressurized to be integrated. A single, alloy or composite metal foil of copper, aluminum, brass, nickel, or the like may be used as the metal foil. The conditions for heating and pressuring the laminate are optionally adjusted such that the curable resin composition is cured. However, if the pressure at the pressuring step is too low, bubbles remain inside of the obtained laminate, which may cause reduction in electric properties thereof. Therefore, it is preferable that the laminate is pressurized under the conditions such that the molding property is satisfied.

For example, the temperature, the pressure, and the heating and pressurizing time are adjusted to 160 to 220° C., 49.0 to 490.3 N/cm$^2$ (5 to 50 kgf/cm$^2$), and 40 to 240 minutes, respectively. Further, thus-obtained single layer laminate can be used as an inner layer material to prepare multilayer laminate. In this case, a circuit is formed on the laminate by the additive method, subtractive method or the like and the circuit surface is treated to be blackened with an acid solution to obtain an inner layer material. An insulating layer is formed using the resin sheet, the resin-coated metal foil or the prepreg on the either or both circuit-formed surfaces and a conductive layer is formed on the surface of the insulating layer to form a multilayer board.

When insulating layers are formed using the resin sheets, the resin-coated sheets are provided on the circuit-formed surfaces of a plurality of inner layer materials to obtain a laminate or a resin sheet is provided between the circuit-formed surface of the inner layer material and the metal foil to form a laminate. The laminate is heated and is pressurized to be integrated to provide a cured product of the resin sheet as the insulating layer and a multilayer inner layer material. The same metal foil as that used for a laminate as an inner layer material may be used.

Heat-pressing can be carried out under the same conditions as those for forming inner layer materials. When an insulating layer is formed by coating a resin on a laminate, it is formed by a method generally called the casting method which comprises coating the phosphorus-containing epoxy resin composition or a flame retardant epoxy resin composition comprising the phosphorus-containing epoxy resin as the resin on the circuit-formed surface of the outermost layer so that the coating preferably has a thickness of 5 to 100 μm, and then heating and drying the coating at 100 to 200° C. for 1 to 90 minutes to form the same into a sheet shape. It is preferable that the thickness of the coating after drying is 5 to 80 μm. Via holes or circuits are further formed on the surface of thus-formed multilayer laminate by the additive method or the subtractive method to form a printed-wiring board.

Further, a multilayer laminate having a larger number of layers can be formed by repeating the above techniques using the printed-wiring board as an inner layer material. In addition, when an insulating layer is formed using the resin-coated metal foil, the resin-coated metal foil is positioned such that the resin layer thereof is opposed to the circuit-formed surface of the inner layer material to form a laminate. Further, a cured product of the resin layer of the resin-coated metal foil is formed as an insulating layer and the outer metal foil is formed as a conductive layer by heat-pressuring this laminate to integrate the same. Heat-pressing can be carried out under the same conditions for the formation of the inner layer material.

In addition, when an insulating layer is formed using the prepreg, one or more layers of the prepreg are laminated on the circuit-formed surface of the inner layer material and an outer metal foil is positioned to form a laminate. Further, a cured product of the prepreg is formed as an insulating layer and the outer metal foil is formed as a conductive layer by heat-pressuring this laminate to integrate the same. The same metal foil as that used in the laminate as the inner layer board may be used. Heat-pressing can be carried out under the same conditions for the formation of the inner layer material. Via holes or circuits are further formed on the surface of the thus-formed multilayer laminate by the additive method or the subtractive method to form a printed-wiring board. Further, a multilayer laminate having a larger number of layers can be formed by repeating the above techniques using the printed-wiring board as an inner layer material.

EXAMPLES

The present invention will be specifically explained with reference to Examples and Comparative examples, but is not limited thereto.

The polymer component content in the compound represented by Formula (1) was determined using the gel permeation chromatograph GPC-8220 manufactured by Tosoh Corporation connected to TSK-GEL SuperH4000, Super H3000, and SuperH2000 which were manufactured by Tosoh Corporation in this order as analytical columns. The temperature in a column room was 40° C., an ultraviolet-visible detector was used as a detector, and the measured wavelength was 400 nm. The flow rate of tetrahydrofuran as an eluent was 1 ml/min, and a sample was prepared using a tetrahydrofuran solution containing 1% of the substance represented by Formula (1) for the determination.

When a solution such as filtrate was determined, the solution in an optional amount was measured, and tetrahydrofuran was added such that the p-benzoquinone component accounted for about 1 wt %. In addition, the prepared sample was subjected to analysis immediately after preparation.

An injection volume was determined such that the detector was not saturated and even a broad peak was able to be quantitatively determined. The injection volume in this device was determined to be 200 μl.

In addition, the purity of the compound represented by Formula (3) contained in the phosphorus-containing phenol compound represented by Formula (3) was determined by HPLC. The device of Agilent 1100 series manufactured by Hewlett-Packerd Company and Cadenza CD-C18 CD005 column manufactured by Imtakt Corporation were used. A mixture solution of a buffer of water/acetate/ammonium acetate at 790/10/2 (parts by weight) with tetrahydrofuran/acetonitrile at (a ratio by volume of) 1/1 was used as an eluent. Gradient elution was performed such that the sample measurement was started using the mixture solution accounting for 30% of the eluent and the mixture solution accounted for 80% of the eluent after eight minutes. After that, the mixture solution accounting for 100% of the eluent was used and the measurement was completed after 24 minutes from the measurement start. The measurement was conducted at the flow rate of 1 ml/min by an ultraviolet-visible detector at a wavelength of 266 nm. An injection volume was determined such that the detector was no saturated and even a fine peak was able to be quantitatively determined. The injection volume in this device was determined to be 5 μl.

The phosphorus-containing phenol compound represented by Formula (3) was dissolved in ethylene glycol to prepare a 6 wt % solution and the appearance of the compound was determined using the solution by the APHA colorimetric method (JIS K6901). The yield of the phosphorus-containing phenol compound represented by Formula (3) was calculated, considering the theoretical amount as 100%, based on the added compound represented by Formula (2).

Epoxy resin compositions comprising the phosphorus-containing phenol compound represented by Formula (3) as an essential ingredient were evaluated by the procedural steps below. First, the compound represented by Formula (3), an epoxy resin, a curing agent, and a curing accelerator were added and were sufficiently mixed with the JK homodisper. The obtained curable resin composition was not clear because it comprised fine powders of the compound represented by Formula (3) and the curing agent. 0.1 g of the composition was put on a hot plate at 160° C. and was mixed by a Teflon (registered trademark) stick and the dissolution time required for the fine powders of the compound represented by Formula (3) and the cured product to be dissolved to provide a clear composition and the gelation time-required for the curing reaction to be completed to provide a gel were determined.

The epoxy resin composition comprising the phosphorus-containing phenol compound represented by Formula (3) as an essential ingredient was put into a mold and was cured at 170° C. for 90 minutes. The glass transition temperature, flame retardancy, and the appearance of the obtained cured product were evaluated. The glass transition temperature was determined using TMA/SS120U manufactured by Seiko Instrument Inc. The test for determining flame retardancy was performed, in accordance with the UL-94 standard. The appearance of the cured product was determined by eyes.

A curable resin composition was obtained by dissolving the phosphorus-containing phenol compound represented by Formula (3), an epoxy resin, dicyandiamide (DICY), and 2-ethyl-4-methylimidazole (2E4MZ) in solvents of 2-methoxyethanol and methyl ethyl ketone to prepare a uniform mixture for the evaluation of a laminate. The varnish was stored at a temperature of 60° C. for 24 hours and the presence of the precipitate of the compound represented by Formula 3 was confirmed by eyes. 0.2 ml of this curable resin composition was put on the hot plate at 160° C. and was mixed by a Teflon (registered trade mark) stick to determine the varnish gelation time required for the curing reaction to be completed to provide a gel. In addition, this curable resin composition was immersed in glass cloth (WEA 7628 107 XS13, manufactured by NittoBoseki Co., Ltd.) and was dried using a circulating hot air oven at 150° C. for seven minutes to obtain a semicured prepreg. Four layers thereof were laminated and copper foils (3EC-III manufactured by Mitsui Kinzoku Kozan Co., Ltd) were interposed. Curing thereof was carried out using a vacuum hot pressing device under a reduced pressure at 170° C. for 70 minutes at a pressure of 20 kgf/cm$^2$. The test for determining flame retardancy was performed, in accordance with the UL-94 standard.

Example 1

60.00 parts by weight of HCA (3,4,5,6-dibenzo-1,2-oxaphosphan-2-oxide, manufactured by Sanko K.K.) as the phosphorus-containing phenol compound represented by Formula (3) and 140 parts by weight of toluene were charged into a five-necked glass separable flask equipped with a stirrer, a thermometer, a cooling tube, a nitrogen inlet and an inlet for charging materials. The mixture was agitated under nitrogen atmosphere and was heated and dissolved at 80° C. 30.30 parts by weight of PBQ (p-benzoquinone, manufactured by Yancheng Fengyang Chemical Industry Co., Ltd.) as the compound represented by Formula (1) and 270 parts by weight of toluene were added into another flask and were dissolved at 20° C. The PBQ powders before the dissolution step were used to prepare a 1% solution thereof and peak area (B) was determined to be 13.2 area %. The toluene solution of benzoquinone was filtered by a membrane filter having a pore size of 1 μm and was charged into the HCA toluene solution over two hours, and then the reaction was conducted at 80° C. for 30 minutes. After 30 minutes, the temperature was raised to the reflux temperature of toluene and the reaction was conducted under the condition for 90 minutes.

Figure 1:
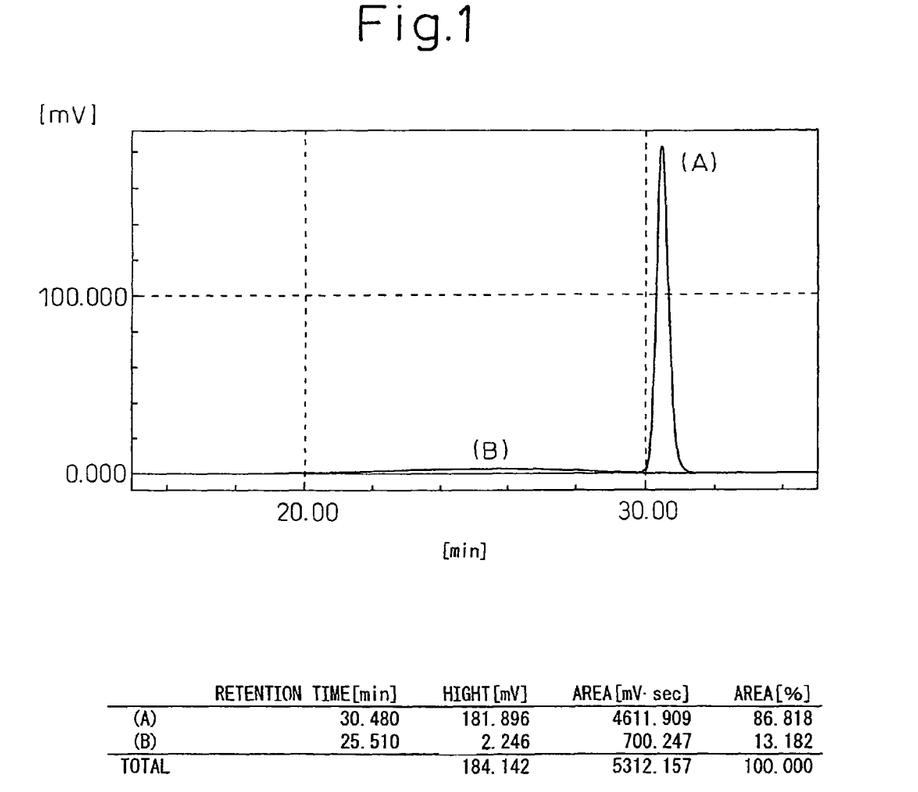
FIG. 1 shows a chromatogram of gel permeation chromatography of PBQ powders.
Figure 2:
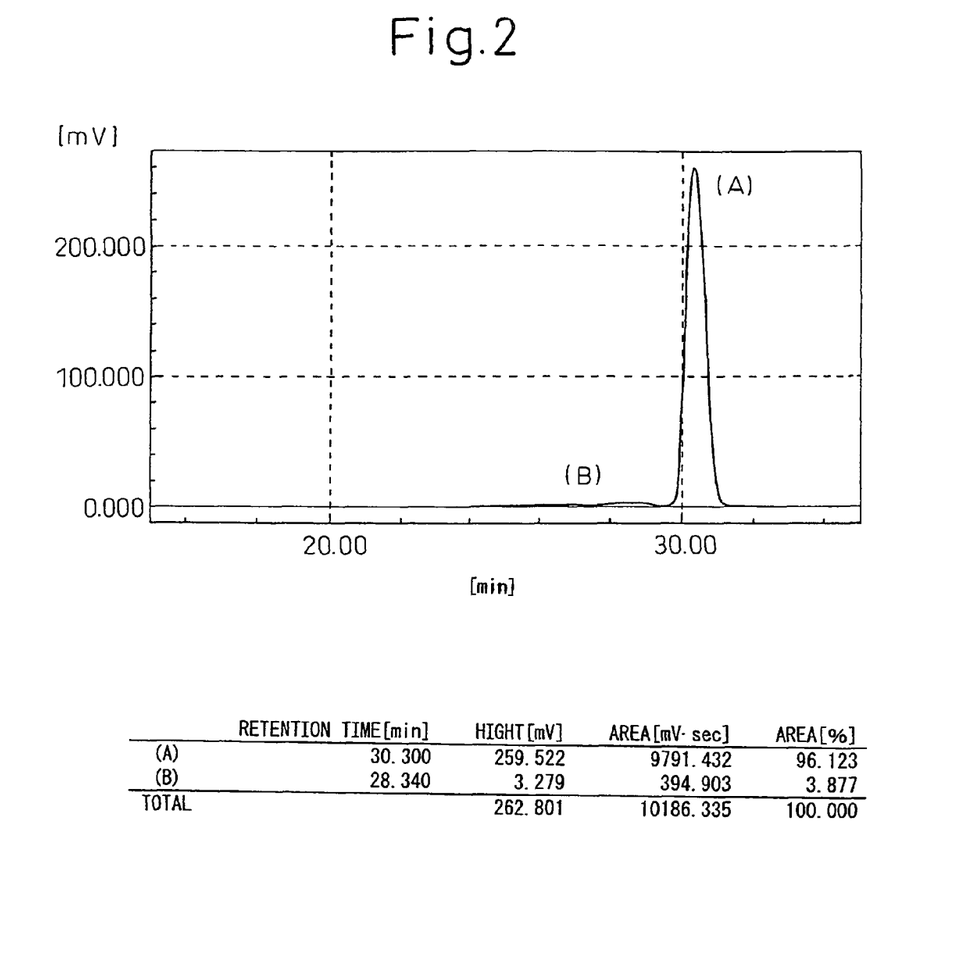
FIG. 2 shows a chromatogram of gel permeation chromatography of filtrate obtained by filtering a PBQ solution.

The solution was gradually cooled and was filtered at 70° C. after the reaction was completed. This was washed with toluene and was dried to obtain white powders of the phosphorus-containing phenol compound. The color thereof was determined to correspond to APHA50. The PBQ filtrate was used to prepare a tetrahydrofuran solution containing 1% of PBQ. Peak area (B) was determined to be 3.9 area %. In addition, the HPLC purity of the obtained phosphorus-containing phenol compound was 98.5% and the yield thereof was 93.5%. FIG. 1 shows a chromatograph of gel permeation chromatography of PBQ powders. FIG. 2 shows a chromatograph of gel permeation chromatography of filtrate of the PBQ solution.

Example 2

The same procedural steps as in Synthesis example 1 were performed except that filtration of PBQ was carried out using a membrane filter having a pore size of 10 μm to obtain white powders of the phosphorus-containing phenol compound. The color thereof was determined to correspond to APHA120. The PBQ filtrate was used to prepare a tetrahydrofuran solution containing 1% of PBQ and peak area (B) was determined to be 4.4 area %. The PBQ powders were used to prepare the 1% solution and peak area (B) was determined to be 13.3 area %. In addition, the HPLC purity of the obtained phosphorus-containing phenol compound was 98.6% and the yield thereof was 93.0%.

Example 3

The same procedural steps as in Synthesis example 1 were performed except that filtration of PBQ was carried out using a membrane filter having a pore size of 20 μm to obtain light brown powders of the phosphorus-containing phenol compound. The color thereof was determined to correspond to APHA200. The PBQ filtrate was used to prepare a tetrahydrofuran solution containing 1% of PBQ and peak area (B) was determined to be 6.9 area %. The PBQ powders were used to prepare the 1% solution and peak area (B) was determined to be 13.3 area %. In addition, the HPLC purity of the obtained phosphorus-containing phenol compound was 98.4% and the yield thereof was 93.4%.

Comparative Example 1

60.00 parts by weight of HCA and 410 parts by weight of toluene were charged into a five-necked glass separable flask equipped with a stirrer, a thermometer, cooling tube, a nitrogen inlet and an inlet for charging materials. The mixture was agitated under nitrogen atmosphere and was dissolved at 80° C. 30.30 parts by weight of PBQ was charged without a purification step, and the temperature of the mixture was raised to the reflux temperature of toluene after 30 minutes, and the reaction was conducted under the condition for 90 minutes. The same procedural steps were performed as in Synthesis example 1 to obtain brown powders of the phosphorus-containing phenol compound. The color thereof was determined to correspond to APHA450. PBQ was used to prepare a tetrahydrofuran solution containing 1% of PBQ and peak area (B) was determined to be 13.3 area %. In addition, the HPLC purity of the obtained phosphorus-containing phenol compound was 92.4% and the yield thereof was 93.8%. The appearance of the powders was brown and black aggregated particles were contained.

Comparative Example 2

54.00 parts by weight of HCA and 120 parts by weight of toluene were charged into the same apparatus as that used in Synthesis example 1 and the mixture was heated and dissolved at 80° C. After HCA was completely dissolved, 24.30 parts by weight of PBQ in powder form divided into a small amount was charged over two hours, and then the reaction was conducted at 130° C. for 120 minutes. After 120 minutes, the mixture was cooled to 20° C. and filtration thereof was performed. The filtrate was washed with 180 parts by weight of ethyl cellosolve, and then was washed with 180 parts by weight of methanol, and was dried to obtain brown powders of the phosphorus-containing phenol compound. 700 parts by weight of methyl cellosolve was added, was heated at 110° C. to dissolve the powders, was cooled to −18° C., and was recrystallized and washed to obtain white powders of the phosphorus-containing phenol compound. The color of the obtained phosphorus-containing phenol compound was determined to correspond to APHA50, the purity thereof was 99.8%, and the yield thereof was 52.2%.

In Example 4 and Comparative examples 3 and 5, after the resin compositions having the formulations described in Table 2 were prepared and the preparations were subjected to a roll dispersion treatment to obtain cured resin compositions. The cured resin compositions were charged into molds and were subjected to a two-step heating process at 130° C. for one hour and at 180° C. for three hours to obtain cured products.

In Example 5 and Comparative examples 6 tO 8, an epoxy resin, a solvent, and the compound represented by Formula 3 added in accordance with the formulation conditions described in Table 3 were heated and were dissolved. After the mixtures were cooled to 60° C., dicyandiamide (DICY) powders were charged and were dissolved. After the powders were completely dissolved, 2E4MZ was added to prepare uniform mixtures to obtain varnishes of curable resin compositions.

Table 1 shows the appearances, purity and yields of the phosphorus-containing phenol compounds obtained in Examples 1 to 3 and Comparative examples 1 and 2. Table 2 shows the solubility and curing reactivity of the phosphorus-containing phenol compounds represented by Formula (3) and/or the DICY powders and physical properties and the appearances of the cured products. Table 3 shows crystallization properties and curing reactivity of the phosphorus-containing phenol compounds represented by Formula (3) in the varnishes of the curable resin compositions obtained in Example 5 and Comparative examples 6 to 8 and heat resistance and flame retardancy thereof contained in laminates.

TABLE 1

Phosphorus-containing phenol compounds

| | | Example 1 (A) | Example 2 (B) | Example 3 (C) | Comparative Example 1 (D) | Comparative Example 2 (E) |
|---|---|---|---|---|---|---|
| Compound of Formula 1 | Parts by weight | 30.3 | 30.3 | 30.3 | 30.3 | 24.3 |
| Compound of Formula 2 | Parts by weight | 60.0 | 60.0 | 60.0 | 60.0 | 54.0 |
| Purification step for Compound of Formula 1 | Present or absent | Present | Present | Present | Absent | Absent |
| Polymer content after the purification step for Compound of Formula 1 | Area % | 3.9 | 4.4 | 6.9 | 13.3 | 13.3 |
| Recrystallization step for Compound of Formula 3 after the reaction | Present or absent | Absent | Absent | Absent | Absent | Present |
| Appearance of Compound of Formula 3 | Color *1 | 50 | 120 | 200 | 450 | 50 |
| Purity of Compound of Formula 3 | Wt % | 98.5 | 98.6 | 98.4 | 92.4 | 99.8 |
| Yield (with respect to Compound of Formula 2) | % | 93.5 | 93.0 | 93.4 | 93.8 | 52.2 |

*1: Compound of Formula 3 was heated and was dissolved in ethylene glycol and the color of a 6 wt % solution was used for the determination by the APHA colorimetric method.

TABLE 2

Formulations of curable resin compositions

| | | Example 4 | Comparative Example 3 | Comparative Example 4 | Comparative Example 5 |
|---|---|---|---|---|---|
| YDF-170 *1 | Parts by weight | 50.00 | 50.00 | 50.00 | 50.00 |
| YDPN-638 *2 | Parts by weight | 50.00 | 50.00 | 50.00 | 50.00 |
| Compound of Formula 3 (A) | Parts by weight | 30.00 | — | — | — |
| Compound of Formula 3 (D) | Parts by weight | — | 30.00 | — | — |
| Compound of Formula 3 (E) | Parts by weight | — | — | 30.00 | — |
| DICY *3 | Parts by weight | 4.30 | 4.30 | 4.30 | 8.12 |
| 2E4MZ *4 | Parts by weight | 0.10 | 0.10 | 0.10 | 0.10 |
| Phosphorus content | Wt % | 2.2 | 2.2 | 2.2 | 0.0 |
| Dissolution time *5 | Second | 321 | 355 | 402 | 10 |
| Gelation time *6 | Second | 405 | 601 | 557 | 210 |
| Glass transition temperature | ° C. | 139 | 128 | 136 | 131 |
| Flame retardancy | UL-94 | V-0 | V-0 | V-0 | Flammable |
| Appearance of cured product | Color | pale yellow | Brown | Pale yellow | Pale yellow |
| | Turbidity | None | Present | None | None |

*1: A BPF type epoxy resin manufactured by Tohto Kasei Co., Ltd.
*2: A phenol novolac type epoxy resin manufactured by Tohto Kasei Co., Ltd.
*3: Dicyandiamide manufactured by Nippon Carbide Industries Co., Inc.
*4: 2-Ethyl-4-methylimidazole manufactured by Shikoku Chemicals Corporation.
*5: The time required for the compound represented by Formula 3 and DICY to be dissolved to provide a clear composition which was determined using a hot plate at 160° C.
*6: The time required for gelation which was determined using a hot plate at 160° C.

TABLE 3

Evaluations in the form of varnishes

| | | Example 5 | Comparative Example 6 | Comparative Example 7 | Comparative Example 8 |
|---|---|---|---|---|---|
| FX-289B *1 | Parts by weight | 50.00 | 50.00 | 50.00 | 50.00 |
| ESN-485 *2 | Parts by weight | 50.00 | 50.00 | 50.00 | 50.00 |
| Methyl ethyl ketone | Parts by weight | 25.00 | 25.00 | 25.00 | 25.00 |
| Compound of Formula 3 (A) | Parts by weight | 7.00 | — | — | — |
| Compound of Formula 3 (D) | Parts by weight | — | 7.00 | — | — |
| Compound of Formula 3 (E) | Parts by weight | — | — | 7.00 | 5.00 |
| DICY *3 | Parts by weight | 3.05 | 3.05 | 3.05 | 3.18 |
| Methyl cellosolve | Parts by weight | 100.00 | 100.00 | 100.00 | 100.00 |
| 2E4MZ *4 | Parts by weight | 0.10 | 0.10 | 0.10 | 0.10 |
| Phosphorus content in resin | Wt % | 1.8 | 1.8 | 1.8 | 1.6 |
| Precipitates of compound represented by Formula 3 *5 | Present or absent | Absent | Absent | Present | Absent |
| Varnish gelation time | Second | 320 | 450 | 366 | 371 |
| Glass transition temperature | ° C. | 155 | 134 | 149 | 142 |
| Flame retardancy | UL-94 | V-0 | V-0 | V-0 | V-1 |

*1: A phosphorus-containing epoxy resin with a phosphorus content of 2% and an epoxy equivalent of 308 g/eq manufactured by Tohto Kasei Co., Ltd.
*2: A naphthol aralkyl type epoxy resin with an epoxy equivalent of 296 g/eq manufactured by Tohto Kasei Co., Ltd.
*3: Dicyandiamide manufactured by Nippon Carbide Industries Co., Inc.
*4: 2-Ethyl-4-methylimidazole manufactured by Shikoku Chemicals Corporation.
*5: Confirmed by eyes after stored at 60° C. for 24 hours.

Industrial Applicability

The synthesis results of the compound represented by Formula 3 are shown in Table 1. The phosphorus-containing phenol compound could be obtained with high purity and in high yield by reacting the compound represented by Formula (1) whose value of peak area (B) is 8 area % or less with the compound represented by Formula (2) in Examples 1 to 3. It was clear that the purity of the phosphorus-containing phenol compound was higher and the appearance thereof was more excellent, compared with those of Comparative example 1 using the compound represented by Formula (1) without having being subjected to a purification step.

Regarding Comparative example 2 which had been subjected to a recrystallization step, that having an excellent color and extremely high purity could be obtained, but the yield thereof was about 52%. As the yield of the compound obtained by the production method of the present invention is 93% or more, it can be understood that the present invention is a production method by which the phosphorus-containing phenol compound represented by Formula (3) can be obtained in high yields. In addition, epoxy resin compositions comprising the phosphorus-containing phenol compound represented by Formula (3) as an essential ingredient which was obtained by the production method of the present invention are described in Tables 2 and 3. Comparing Example 4 with Comparative example 3, and Example 5 with Comparative example 6, it is presumed that when the phosphorus-containing phenol compound (D) represented by Formula (3) with low purity was used, the reactivity was decreased and the gelation time was prolonged, due to the presence of impurity components.

Further, it can be understood that the heat resistance of the cured products was reduced and the appearance thereof became bad. Comparison of Example 4 with Comparative example 4 shows there was a difference in dissolution time. Comparison of Example 5 with Comparative example 7 shows that the phosphorus-containing phenol compound represented by Formula (3) was precipitated in the form of crystals in the varnish. Therefore, it is presumed that it is likely that a uniformly cured product cannot be obtained using the phosphorus-containing phenol compound (E) represented by Formula (3). It is presumed to be the cause therefor that the phosphorus-containing phenol compound (E) represented by Formula (3) exhibits a strong crystalline property because it was subjected to a recrystallization step and exhibits poor solubility, and thus it takes a long time for the curing reaction to be completed.

Further, when the phosphorus-containing phenol compound represented by Formula (3) is not used as in Comparative example 5, flame retardancy cannot be obtained. When the phosphorus-containing phenol compound represented by Formula (3) is used in such an amount that it is not precipitated in the form of crystals in the varnish as in Comparative example 8, sufficient flame retardancy cannot be obtained. It can be understood from the above that the phosphorus-containing phenol compound represented by Formula (3) of the present invention can be obtained with high purity and in high yield and exhibits excellent solubility in epoxy resin compositions.

The invention claimed is:

1. A composition comprising a phosphorus-containing phenol compound represented by Formula (3), said composition is obtained by reacting a compound represented by Formula (2) with a composition comprising a compound represented by Formula (1), wherein on a chromatogram of the composition comprising the compound represented by Formula (1) measured by gel permeation chromatography peak area (A), peak area (B) on the high-molecular-weight side of the component of (A), and total area (C) of peak area (A) and peak area (B) satisfy the condition that the value obtained by dividing peak area (B) by total area (C) is 8 area % or less;

wherein the gel permeation chromatography is carried out under the conditions:

an analytical column having an exclusion limit molecular weight of 400,000, a number of theoretical stages of 16,000, and a length of 30 cm, an analytical column having an exclusion limit molecular weight of 60,000, a number of theoretical stages of 16,000, and a length of 30 cm, and an analytical column having an exclusion limit molecular weight of 10,000, a number of theoretical stages of 16,000, and a length of 30 cm connected in series are used, the temperature in a column room is adjusted to 40° C., an ultraviolet-visible detector is used as a detector, the measured wavelength is 400 nm, the flow rate of tetrahydrofuran as an eluent is 1 ml/min, and a sample is prepared using a tetrahydrofuran solution containing 1% of the compound represented by Formula (1) for the determination Formula (1)

Formula (2)

Formula (3)

2. A curable resin composition comprising the phosphorus-containing phenol composition according to claim 1 as an essential ingredient and an epoxy resin.

3. A method for producing a phosphorus-containing phenol compound represented by Formula (3):

Formula (3)

comprising the steps of:
(i) filtering a solution of a compound represented by Formula (1):

Formula (1)

so that on a chromatogram measured by gel permeation chromatography peak area (A), peak area (B) on the high-molecular-weight side of the component of (A), and total area (C) of peak area (A) and peak area (B) satisfy the condition that the value obtained by dividing peak area (B) by total area (C) is 8 area % or less;
wherein the gel permeation chromatography is carried out under the conditions:
an analytical column having an exclusion limit molecular weight of 400,000, a number of theoretical stages of 16,000, and a length of 30 cm, an analytical column having an exclusion limit molecular weight of 60,000, a number of theoretical stages of 16,000, and a length of 30 cm, and an analytical column having an exclusion limit molecular weight of 10,000, a number of theoretical stages of 16,000, and a length of 30 cm connected in series are used,
the temperature in a column room is adjusted to 40° C.,
an ultraviolet-visible detector is used as a detector,
the measured wavelength is 400 nm,
the flow rate of tetrahydrofuran as an eluent is 1 ml/min, and
a sample is prepared using a tetrahydrofuran solution containing 1% of the compound represented by Formula (1) for the determination; and
(ii) reacting the compound represented by Formula (1) obtained in step (i) with a compound represented by Formula (2):

Formula (2)

to obtain the phosphorus-containing phenol compound represented by Formula (3).

4. A curable resin composition comprising the phosphorus-containing phenol compound obtained by the method according to claim 3 as an essential ingredient and an epoxy resin.

5. A cured product prepared by curing the curable resin composition according to claim 2 or 4.

* * * * *

UNITED STATES PATENT AND TRADEMARK OFFICE
CERTIFICATE OF CORRECTION

PATENT NO. : 8,609,806 B2
APPLICATION NO. : 12/998078
DATED : December 17, 2013
INVENTOR(S) : Tetsuya Nakanishi et al.

It is certified that error appears in the above-identified patent and that said Letters Patent is hereby corrected as shown below:

In the Specification

Column 8, line 28, change "FX 289B" to -- FX-289B --;

Column 12, line 43, change "Formula 3" to -- Formula (3) --;

Column 14, line 2, change "30 30" to -- 30.30 --;

Column 14, line 47, change "6 tO 8" to -- 6 to 8 --;

Column 17, line 2-3, change "Formula 3" to -- Formula (3) --;

In the Claims

Column 18, line 38-49, change "  " to -- --.

Signed and Sealed this
Twelfth Day of August, 2014

Michelle K. Lee
*Deputy Director of the United States Patent and Trademark Office*